(12) United States Patent
Bissmann

(10) Patent No.: US 8,480,661 B2
(45) Date of Patent: Jul. 9, 2013

(54) APPARATUS AND METHOD FOR REMOVING A LENTICLE FROM THE CORNEA

(75) Inventor: Wilfried Bissmann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/260,187

(22) PCT Filed: Mar. 27, 2010

(86) PCT No.: PCT/EP2010/001951
§ 371 (c)(1),
(2), (4) Date: Sep. 23, 2011

(87) PCT Pub. No.: WO2010/112184
PCT Pub. Date: Oct. 7, 2010

(65) Prior Publication Data
US 2012/0016353 A1    Jan. 19, 2012

(30) Foreign Application Priority Data
Apr. 3, 2009 (DE) .................. 10 2009 015 911

(51) Int. Cl.
*A61B 18/20* (2006.01)

(52) U.S. Cl.
USPC .................................. 606/5; 606/4; 128/898

(58) Field of Classification Search
USPC ......................................... 128/898; 606/4, 5
See application file for complete search history.

(56) References Cited

U.S. PATENT DOCUMENTS

| | | |
|---|---|---|
| 3,589,363 A | 6/1971 | Banko et al. |
| 3,982,541 A | 9/1976 | L'Esperance, Jr. |
| 5,496,342 A | 3/1996 | Urich |
| 5,885,243 A | 3/1999 | Capetan et al. |
| 5,984,916 A | 11/1999 | Lai |
| 6,013,049 A | 1/2000 | Rockley et al. |
| 6,110,116 A | 8/2000 | Wright et al. |
| 6,461,349 B1 | 10/2002 | Elbrecht et al. |
| 6,620,154 B1* | 9/2003 | Amirkhanian et al. ......... 606/17 |
| 7,351,241 B2 | 4/2008 | Bendett et al. |
| 2004/0167556 A1* | 8/2004 | Chuck ........................ 606/167 |
| 2004/0243111 A1* | 12/2004 | Bendett et al. ................ 606/5 |
| 2006/0047254 A1 | 3/2006 | Akahoshi |
| 2006/0195075 A1 | 8/2006 | Muhlhoff et al. |
| 2008/0275433 A1 | 11/2008 | Russmann et al. |
| 2008/0281277 A1 | 11/2008 | Thyzel |
| 2008/0319428 A1 | 12/2008 | Wiechmann et al. |

FOREIGN PATENT DOCUMENTS

| | | |
|---|---|---|
| DE | 19 52 574 | 12/1966 |
| DE | 197 47 046 A1 | 5/1999 |
| DE | 697 18 671 T2 | 12/2003 |
| DE | 10 2005 008 235 A1 | 8/2006 |
| DE | 10 2006 053 118 A1 | 5/2008 |
| DE | 10 2007 019 813 A1 | 10/2008 |
| EP | 1 632 205 A1 | 3/2006 |
| EP | 1 849 443 A1 | 10/2007 |
| WO | WO 02/07659 A2 | 1/2002 |

(Continued)

*Primary Examiner* — Bill Thomson
*Assistant Examiner* — Jeffrey Lipitz
(74) *Attorney, Agent, or Firm* — Patterson Thuente Pedersen, P.A.

(57) ABSTRACT

An apparatus and method for removing a lenticle from the cornea. For this purpose, a device for liquefying the lenticle and a device for suctioning off the resulting fluid are provided. The lenticle is liquefied and the resulting fluid is then suctioned off.

4 Claims, 3 Drawing Sheets

FOREIGN PATENT DOCUMENTS

| | | |
|---|---|---|
| WO | WO 02/056806 A1 | 7/2002 |
| WO | WO 2004/105671 A1 | 12/2004 |
| WO | WO 2005/011545 A1 | 2/2005 |
| WO | WO 2005/092258 A1 | 10/2005 |

* cited by examiner

APPARATUS AND METHOD FOR REMOVING A LENTICLE FROM THE CORNEA

PRIORITY CLAIM

The present application is a National Phase entry of PCT Application No. PCT/EP2010/001951, filed Mar. 27, 2010, which claims priority from German Application No 102009015911.8, filed Apr. 3, 2009, the disclosures of which are hereby incorporated by reference herein in their entirety.

FIELD OF THE INVENTION

The invention relates to a device and a method for removing a lenticle from the cornea of the eye. Such a lenticle forms when appropriate cut surfaces are created through sequencing optical breakthroughs in the cornea by means of focused laser radiation, wherein the focal point is preferably adjusted three-dimensionally.

BACKGROUND

Thereto, treatment laser radiation is focused within the corneal tissue, i.e., below the tissue surface, in such a way that optical breakthroughs occur in the tissue.

Thereby, a number of processes take place in temporal sequence which are initiated by the laser radiation. If the power density of the radiation exceeds a threshold, an optical breakthrough occurs which produces a plasma bubble in the material. After the optical breakthrough occurs, said plasma bubble grows due to expanding gases. If the optical breakthrough is not maintained, the gas produced in the plasma bubble is absorbed by the surrounding material and the bubble disappears. However, this process takes very much longer than the forming of the bubble. If plasma is produced at a material boundary layer, which can also lie within a material structure, a material removal from the boundary layer occurs.

This is called photoablation. In the case of a plasma bubble, which separates previously connected material layers, it is usually called photodisruption. For reasons of simplification, all such processes shall herein be combined under the term optical breakthrough, i.e., said term not only includes the actual optical breakthrough but also the resulting effects in the material.

For great accuracy of a laser-surgical method it is absolutely essential to ensure high localization of the effect of the laser beams and to avoid collateral damages in the adjacent tissue as much as possible. Therefore, it is customary in prior art to apply pulsed laser radiation, wherein the threshold value for the power density, required for the triggering of an optical breakthrough, is exceeded only in the individual pulses. In this respect, U.S. Pat. No. 5,984,916 clearly shows that the spatial area of the optical breakthrough (in this case, the produced interaction) greatly depends on the pulse duration.

A high focusing of the laser beam in combination with very short pulses in the femtosecond range therefore allows for a precisely accurate introduction of the optical breakthrough in the material.

The use of pulsed laser radiation has recently become generally accepted particularly in ophthalmology for the laser-surgical correction of defective vision.

Defective vision of the eye is frequently caused because the diffractive properties of cornea and lens do not effect optimal focusing on the retina.

The above-mentioned U.S. Pat. No. 5,984,916 as well as U.S. Pat. No. 6,110,166 describe methods for producing incisions by means of a suitable creation of optical breakthroughs with the use of fs lasers; as a result, the refractive properties of the cornea can eventually be specifically affected. A multitude of optical breakthroughs is sequenced in such a way that a lenticular partial volume (lenticle) is isolated within the cornea of the eye. Then the lenticular partial volume, separated from the remaining corneal tissue, is removed from the cornea through a laterally opening incision. The shape of the lenticle is selected so that after removal, the form and therefore the refractive properties of the cornea are altered in such a way that the desired correction of the defective vision is effected. The cut surfaces required thereto are curved which requires a three-dimensional adjustment of the focus. Therefore, a two-dimensional deflection of the laser radiation is thereto combined with a simultaneous focus adjustment in a third spatial direction. In order to remove the lenticle, the opening incision must be relatively large, generally almost as large as the diameter of the lenticle, or even in the form of a flap, i.e., a thin slice of the cornea which is folded back in order to remove the lenticle positioned below.

In DE 10 2007 019 813 by the applicant, it was suggested that only relatively small opening incisions but, in return, a plurality of opening incisions be provided and the lenticle be removed through said incisions. However, this has proven relatively difficult because the lenticle, despite its small thickness (max. 200 μm), exhibits a certain stiffness which makes it difficult to remove the lenticle through the small opening incisions.

WO 2004/105661 describes another type of lenticle removal, wherein the lenticle is cut into small fragments by means of the fs laser (i.e., the treatment laser) in such a way that said fragments can be suctioned off by means of one or more cannulas. As a result, a smaller incision for inserting the cannula and/or cannulas suffices in comparison to the removal of the entire lenticle. However, for this purpose, the lenticle must be cut very accurately into very small pieces which significantly prolongs the duration of treatment during which the eye must be kept immobilized relative to the treatment laser in order to correctly perform the incisions.

SUMMARY OF THE INVENTION

Therefore, the invention addresses the problem of providing a device and a method to significantly simplify the lenticle removal with regard to prior art and to make it less invasive.

According to the invention, this problem is solved through a device for removing a lenticle from the cornea which exhibits an arrangement for liquefying the lenticle and an arrangement for suctioning off the resulting liquid.

The method, according to the invention, is characterized in that the lenticle is liquefied and the resulting liquid is subsequently suctioned off.

According to one example embodiment, the arrangement for liquefying the lenticle exhibits an ultrasound oscillator.

According to another example embodiment, the arrangement for liquefying the lenticle exhibits an arrangement for emitting optical radiation, for example, laser radiation.

Another example embodiment provides an arrangement for introducing a rinsing fluid.

In a first example embodiment of the method, according to the invention, the lenticle is destroyed through ultrasonic oscillations.

Alternatively, the lenticle can be destroyed through optical radiation, particularly laser radiation.

It is particularly advantageous when a rinsing fluid is introduced into the cornea in order to support the removal of the liquefied lenticle parts.

The technical realization of the individual components of the device, according to the invention, is known in principle. They are used for the so-called phacoemulsification of the cataract of the crystalline lens. The phacoemulsification of the lens is known since 1967 (U.S. Pat. No. 3,589,363 by Charles Kelman); this device is based on the use of ultrasound for liquefying the crystalline lens, wherein the resulting liquid is suctioned off and an artificial lens (intraocular lens IOL) is inserted in the resulting cavity. In U.S. Pat. No. 3,982,541 (L'Esperance) it was suggested to execute the liquefying of the cataract of the lens with a ($CO_2$ laser).

Even though there have been continuous advancements of the technique of phacoemulsification, DE 197 47 046 and DE 19 52 574 by the applicant, inter alia, the complete contents of which are incorporated by reference, a utilization of said technique for the removal of another part of the eye (i.e., parts of the cornea, as suggested herein) has never been envisaged.

BRIEF DESCRIPTION OF THE DRAWINGS

In the following, the invention is still further explained with reference to the drawing by way of example.

DETAILED DESCRIPTION

Figure 1:
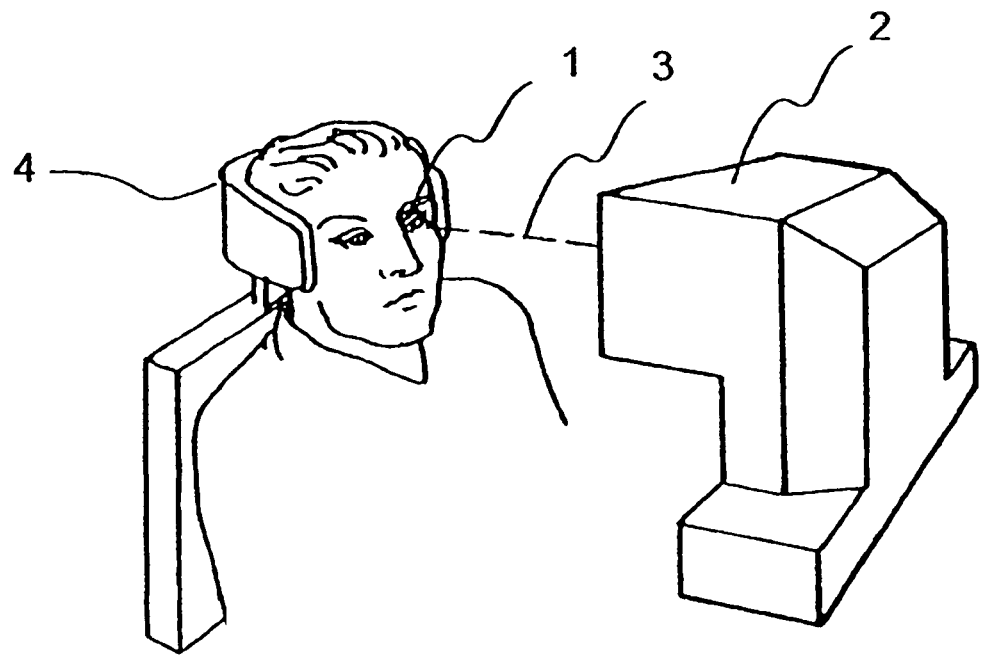
FIG. 1 is a perspective depiction of a patient during a laser-surgical treatment with a laser-surgical instrument.

FIG. 1 shows a laser-surgical instrument for the treatment of an eye 1 of a patient, wherein the laser-surgical instrument 2 is used for performing a refractive correction. Thereto, the instrument 2 emits a treatment laser beam 3 onto the eye of the patient 1, the head of which is immobilized in a headrest 4. The laser-surgical instrument 2 is capable of producing a pulsed laser beam 3, e.g., in order to perform the method described in U.S. Pat. No. 6,110,166.

Figure 2:
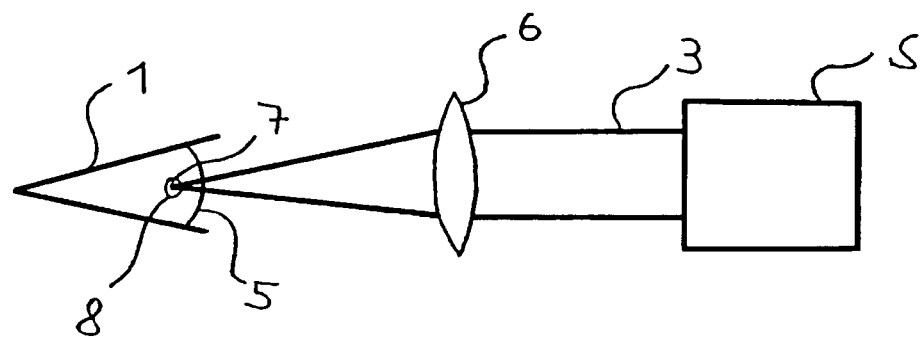
FIG. 2 depicts the focusing of a beam onto the eye of the patient with the instrument in FIG. 1.

Thereto, the laser-surgical instrument 2 exhibits, as shown schematically in FIG. 2, a beam source S, the radiation of which is focused in the cornea 5 of the eye 1. By means of the laser-surgical instrument 2, the defective vision of the eye 1 of the patient can be corrected in such a way that material is removed from the cornea 5, thereby effecting the change of the refractive properties of the cornea by a desired degree. Thereby, the material is removed from the stroma of the cornea, which lies below the epithelium and Bowman's membrane and above Descemet's membrane and the endothelium. Alternatively, it is also possible to perform only one incision with the laser-surgical instrument 2 in the cornea for the preparation of a flap.

The material removal and/or separation is executed, wherein tissue layers in the cornea are separated through focusing of the high-energy fs laser beam 3 by means of an objective telescope 6 in a focus 7 in the cornea 5. Thereby, every pulse of the pulsed laser radiation 3 produces an optical breakthrough in the tissue, initiating a plasma bubble 8.

As a result, the separation of the tissue layer encompasses a larger area than the focus 7 of the laser radiation 3. Through appropriate deflection of the laser beam 3, a great number of plasma bubbles 8 are now sequenced during the treatment. Subsequently, the contiguous plasma bubbles 8 form a cut surface 16.

Due to the laser radiation 3, the laser-surgical instrument 2 acts as a surgical knife which directly separates material layers in the interior of the cornea 5 without harming the surface of the cornea 5. If the incision is carried out all the way to the surface of the cornea 5 (opening incision) through producing further plasma bubbles 8, a material of the cornea 5, which was isolated through the cut surface 16, can be removed, wherein the flap is partially lifted and folded back.

Figure 3:
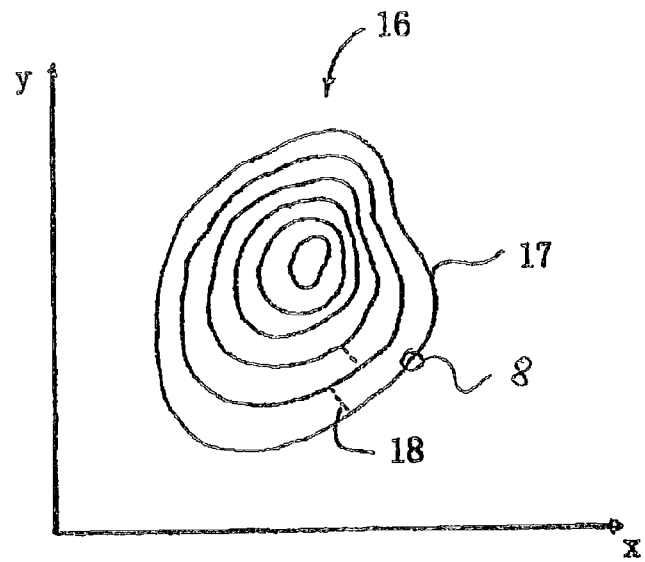
FIG. 3 is an exemplary image of the line of incision.

The generation of a cut surface 16 by means of the laser-surgical instrument 2 is shown schematically in FIG. 3. A cut surface 16 is formed through the sequencing of the plasma bubbles 8 as a result of a continuous shift of the focus 7 of the pulsed laser beam 3 along the cutting line 17. In order to remove a partial volume, two such cut surfaces 16, 16' must be formed in a suitable geometric assignment to one another and in a suitable form.

Thereby, the focus shift takes place in an embodiment by means of a deflection unit (not depicted in FIG. 2) in x- and y-direction, and the telescope 6 is appropriately adjusted for control in z-direction. As a result, the focus 7 can be adjusted along three orthogonal axes.

For generating the cut surface 16, the focus 7 is now adjusted through the deflection unit in accordance with the cutting lines 17, wherein the zoom optics 6 can, for every cutting line 17, adjust a corresponding z-coordinate for the focus 7. While the focus 7 moves over a cutting line 17, the telescope can remain as previously adjusted; if necessary, an adjustment is only required during the junctions 18, shown as dotted line in FIG. 3, between adjacent cutting lines 17.

Figure 4:
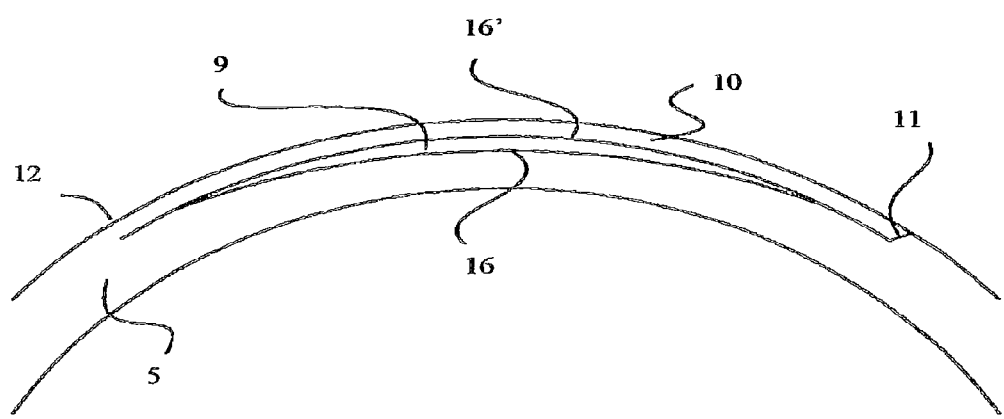
FIG. 4 is a cross-section of the cornea with a lenticle.

FIG. 4 shows a cross-section of the cornea 5 after the cutting of two cut surfaces 16, 16' for isolating a lenticle 9. The lenticle 9 is still covered by the flap 10, which is bounded by a peripheral incision (opening incision) 11. The peripheral incision 11 is performed in such a way that a part of the corneal tissue is not separated and remains as a hinge 12. This ensures that the flap 10 is not completely separated and can therefore be repositioned more easily.

Figure 5:
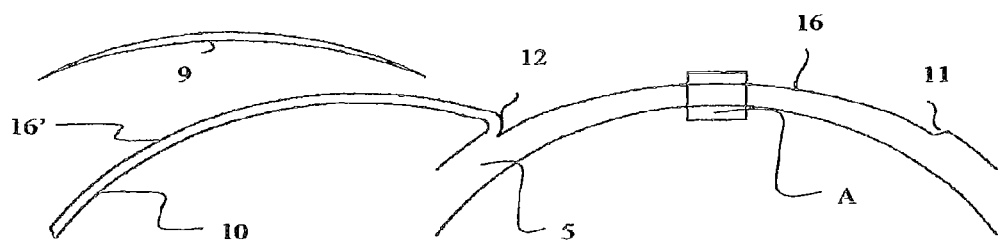
FIG. 5 is a cross-section of the cornea after removal of the lenticle, according to prior art.

FIG. 5 shows a cross-section of the cornea 5 with opened flap 10, wherein the lenticle 9 is now removed, according to prior art. The opening incision 11 encompasses almost the entire circumference of the lenticle 9.

Figure 6:
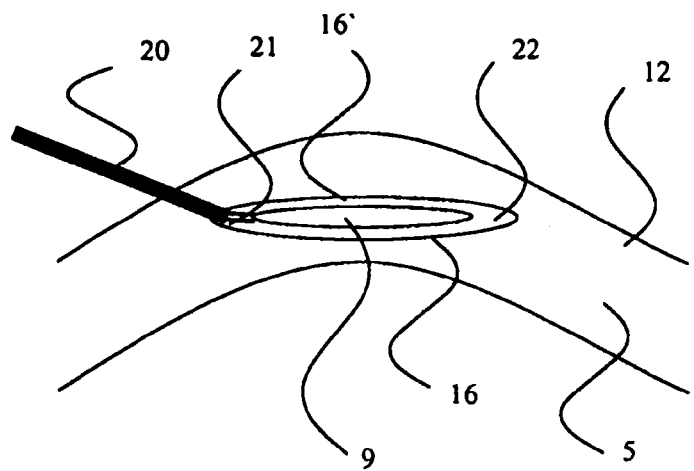
FIG. 6 is a cross-section of the cornea with the device, according to the invention.

FIG. 6 shows the first embodiment of the invention. Hereby, a handpiece 20 with an arrangement 21 for liquefying corneal material is led through a small opening to the lenticle 9. Thereby, the operation of the arrangement for liquefying corneal material can either be ultrasound-based or laser-based. Furthermore, the handpiece 20 exhibits a not depicted arrangement for the suctioning off of the liquefied corneal material of the lenticle. In order to better separate the lenticle 9 from the remaining corneal material 5, a liquid 22 (e.g., base saline solution or BSS) was introduced between the cut surfaces 16, 16' and the lenticle 9 (shown as exaggerated depiction). Through the arrangement 21, the lenticle 9 is sucked in, locally liquefied and suctioned off by means of the handpiece 20. Thereby, the handpiece 20 is moved successively by the surgeon through the space of the lenticle 9, which, as a result, is gradually destroyed and suctioned off. Thereby, this method is particularly advantageous because the eye does not have to be immobilized with µm accuracy as is the case with the method suggested in WO 2004/105661. Furthermore, the surgeon is already familiar with the handling of the handpiece due to the surgeon's experience with lens removals by means of phacoemulsification.

Figure 7:
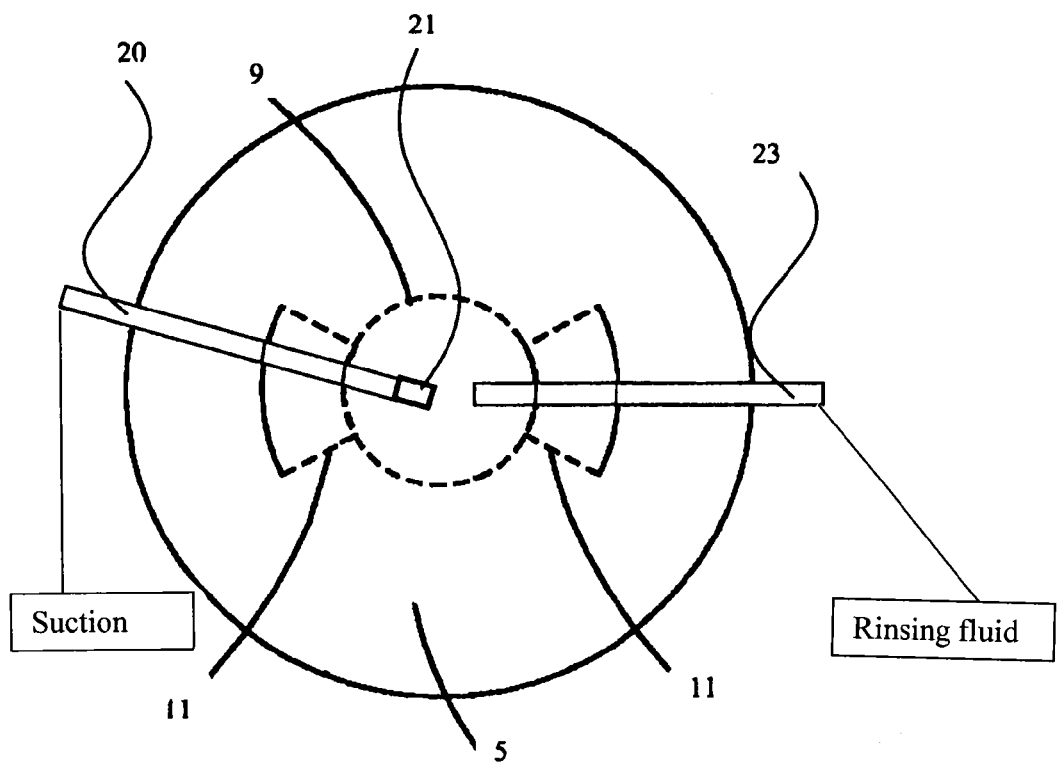
FIG. 7 is a top view of the cornea with a second embodiment of the device, according to the invention.

FIG. 7 shows a broadening of the invention. Hereby, a second handpiece 23 is introduced in the space of the lenticle 9 through a second incision 11, through which rinsing fluid can be introduced even during the operation with the first handpiece 20. This is the so-called bimanual procedure also known from the lens removal procedure. In addition to the rinsing fluid, pharmaceuticals, e.g., to improve the healing process, can also be introduced into the cornea. The peripheral incisions 11 can also be much smaller than depicted in FIG. 7 but must be at least large enough for the introduction of the handpiece 20, 23.

The invention claimed is:

1. A method for removing a lenticle from the cornea, comprising:
   liquefying the lenticle within a stroma of the cornea which lies between Bowman's membrane and Descemet's membrane creating a resulting liquid; and
   subsequently suctioning off the resulting liquid from within the stroma of the cornea.

2. The method for removing a lenticle from the cornea, according to claim 1, further comprising liquefying the lenticle with ultrasound oscillations.

3. The method for removing a lenticle from the cornea, according to claim 1, further comprising liquefying the lenticle with optical radiation.

4. The method for removing a lenticle from the cornea, according to claim 1, further comprising introducing a rinsing fluid into the cornea.

* * * * *